United States Patent
Prior et al.

(10) Patent No.: US 11,090,083 B2
(45) Date of Patent: Aug. 17, 2021

(54) UTERINE MANIPULATORS

(71) Applicant: COVIDIEN LP, Mansfield, MA (US)

(72) Inventors: Scott J. Prior, Shelton, CT (US); Nikolai D. Begg, Wayland, MA (US)

(73) Assignee: Covidien LP, Mansfield, MA (US)

(*) Notice: Subject to any disclaimer, the term of this patent is extended or adjusted under 35 U.S.C. 154(b) by 178 days.

(21) Appl. No.: 16/186,673

(22) Filed: Nov. 12, 2018

(65) Prior Publication Data
US 2019/0150983 A1 May 23, 2019

Related U.S. Application Data

(60) Provisional application No. 62/588,638, filed on Nov. 20, 2017.

(51) Int. Cl.
*A61B 17/42* (2006.01)
*A61B 17/00* (2006.01)
*A61B 90/00* (2016.01)

(52) U.S. Cl.
CPC .......... *A61B 17/4241* (2013.01); *A61B 90/06* (2016.02); *A61B 90/08* (2016.02); *A61B 2017/00115* (2013.01); *A61B 2017/00287* (2013.01); *A61B 2017/00557* (2013.01); *A61B 2017/4225* (2013.01); *A61B 2090/065* (2016.02); *A61B 2090/0807* (2016.02)

(58) Field of Classification Search
None
See application file for complete search history.

(56) References Cited

U.S. PATENT DOCUMENTS

| | | | |
|---|---|---|---|
| 3,938,521 A | 2/1976 | Ritota et al. | |
| 5,645,083 A * | 7/1997 | Essig | A61B 17/00234 128/898 |
| 7,717,312 B2 | 5/2010 | Beetel | |
| 8,696,563 B2 | 4/2014 | Williams et al. | |
| 2013/0138115 A1 | 5/2013 | Seckin | |
| 2014/0052018 A1 | 2/2014 | Hawkins | |
| 2014/0276812 A1* | 9/2014 | Batchelor | A61B 18/1485 606/48 |
| 2014/0288486 A1* | 9/2014 | Hart | A61B 10/04 604/26 |
| 2014/0330285 A1 | 11/2014 | Rosenblatt et al. | |
| 2015/0133923 A1 | 5/2015 | Batchelor et al. | |
| 2015/0272619 A1 | 10/2015 | Zisow | |

(Continued)

*Primary Examiner* — Shaun L David
(74) *Attorney, Agent, or Firm* — Carter, DeLuca & Farrell LLP

(57) ABSTRACT

A uterine manipulator includes a handle assembly and a shaft extending distally from the handle assembly. An end effector assembly is disposed at a distal end portion of the shaft and includes a cervical cup and a distal tip extending distally from the cervical cup. A specimen containment system is supported on the shaft between the handle assembly and the end effector assembly. The specimen containment system includes a sleeve having a proximal end portion and a distal end portion, and a specimen containment bag having a first end portion and a second end portion. The specimen containment bag is supported within the sleeve and is movable from an initial position, wherein the specimen containment bag is disposed within the sleeve, to a deployed position, wherein the specimen containment bag is deployed from the sleeve.

11 Claims, 10 Drawing Sheets

(56) References Cited

U.S. PATENT DOCUMENTS

2015/0297254 A1 10/2015 Sullivan et al.
2016/0302783 A1 10/2016 Greenberg et al.
2019/0059948 A1* 2/2019 Kim ..................... A61B 17/42

* cited by examiner

UTERINE MANIPULATORS

CROSS REFERENCE TO RELATED APPLICATION

The present application claims the benefit of and priority to U.S. Provisional Application Ser. No. 62/588,638, filed on Nov. 20, 2017 the entire contents of which are incorporated herein by reference.

TECHNICAL FIELD

The present disclosure relates to surgical instruments and, more particularly, to uterine manipulators facilitating hysterectomy and other gynecological procedures.

BACKGROUND

One of the final steps in a laparoscopic hysterectomy is a colpotomy, which requires making a circular incision in vaginal tissue to separate the uterus from the vagina. This incision is typically performed with the aid of a uterine manipulator. Uterine manipulators are conventionally used to position the vagina and the cervix to enable removal of the uterus or other tissue specimens after the colpotomy. Typically, uterine manipulators include a handle and a shaft extending distally from the handle that includes a cervical cup and an inflatable balloon. In use, the inflatable balloon is advanced through the vagina and cervix and is positioned within the uterus in a deflated position. Once positioned within the uterus, the inflatable balloon is inflated to secure the uterine manipulator within the uterus and the cervical cup is positioned about the cervix for effectuating the colpotomy.

During a colpotomy procedure, a sufficient distal force must be exerted on the uterine manipulator to mobilize the cervix away from the ureters such that the colpotomy incision can be performed. Applying insufficient force may allow the cervix to return to its anatomical position adjacent to the ureters, which may result in injury to the ureters during the colpotomy.

Following the colpotomy, the uterus is removed and may be first placed in an enclosed environment, e.g., a specimen bag, to inhibit seeding of cancer cells. Typically, the specimen bag is separately inserted, e.g., through an abdominal port, and the uterus is placed in the specimen bag. The uterus may be broken down within the specimen bag, e.g., using a morcellator, to facilitate removal through a minimally-invasive opening.

SUMMARY

Accordingly, a need exists for a uterine manipulator that provides an indication of force and that includes an integrated specimen bag.

According to an aspect of the present disclosure, a uterine manipulator is provided including a handle assembly having a housing, and a shaft extending distally from the handle assembly. An end effector assembly is disposed at a distal end portion of the shaft and includes a cervical cup and a distal tip extending distally from the cervical cup. A specimen containment system is supported on the shaft between the handle assembly and the end effector assembly. The specimen containment system includes a sleeve having a proximal end portion and a distal end portion, and a specimen containment bag defining a first end portion and a second end portion. The specimen containment bag is supported within the sleeve and is movable from an initial position, wherein the specimen containment bag is disposed within the sleeve, to a deployed position, wherein the specimen containment bag is deployed from the sleeve.

In embodiments, the second end portion of the specimen containment bag includes a reinforced rim.

In some embodiments, in the initial position, at least a portion of the reinforced rim is disposed within the sleeve and, in the deployed position, the reinforced rim is disposed externally of the sleeve.

In certain embodiments, the reinforced rim includes a resiliently flexible material.

In embodiments, the reinforced rim is returned under bias towards an at-rest position upon movement of the specimen containment bag to the deployed position.

In some embodiments, the second end portion of the specimen containment bag includes a grasping tab.

In certain embodiments, the specimen containment bag includes a plurality of elongated pockets disposed on an interior surface thereof, each pocket including a resilient finger therein configured to bias the specimen containment bag toward an open condition.

In embodiments, the specimen containment bag is formed from at least one of a transparent, tear-resistant, or stretchable material.

In some embodiments, a shuttle is slidably supported on the shaft and selectively coupled to the cervical cup.

In certain embodiments, an inflatable balloon is supported on the distal end portion of the shaft.

In embodiments, an occluder is slidably supported on the shaft.

According to another aspect of the present disclosure, a uterine manipulator is provided including a handle assembly having a housing, a shaft extending distally from the handle assembly, and an end effector assembly disposed at a distal end portion of the shaft. The end effector assembly includes a cervical cup and a distal tip extending distally from the cervical cup. A biasing element is operably coupled between the housing and the shaft and is configured to enable movement of the housing relative to the shaft.

In embodiments, the biasing element is secured between a proximal end portion of the housing and a proximal end portion of the shaft.

In some embodiments, an outer surface of the housing includes a window and a plurality of markings along a length of the window.

In certain embodiments, the housing includes an indicator disposed on the proximal end portion of the shaft that is viewable through the window.

In embodiments, when the biasing element compresses, the indicator moves through the window and the position of the indicator relative to the plurality of markings provides an indication of a force applied to tissue.

In some embodiments, the housing includes a sensor configured to activate upon a threshold application of force to the handle assembly.

In certain embodiments, the housing includes an alert device configured to alert a user once the threshold application of force is sensed by the sensor.

In embodiments, the alert device produces at least one of auditory, visual, or tactile feedback.

In some embodiments, the sensor includes at least one of a contact sensor, optical sensor, RFID sensor, Ferro-magnetic sensor, magnetic tape sensor, and strain-gauge.

BRIEF DESCRIPTION OF THE DRAWINGS

Objects and features of the present disclosure will become apparent to those of ordinary skill in the art when descriptions thereof are read with reference to the accompanying drawings, of which.

DETAILED DESCRIPTION

Figure 1:
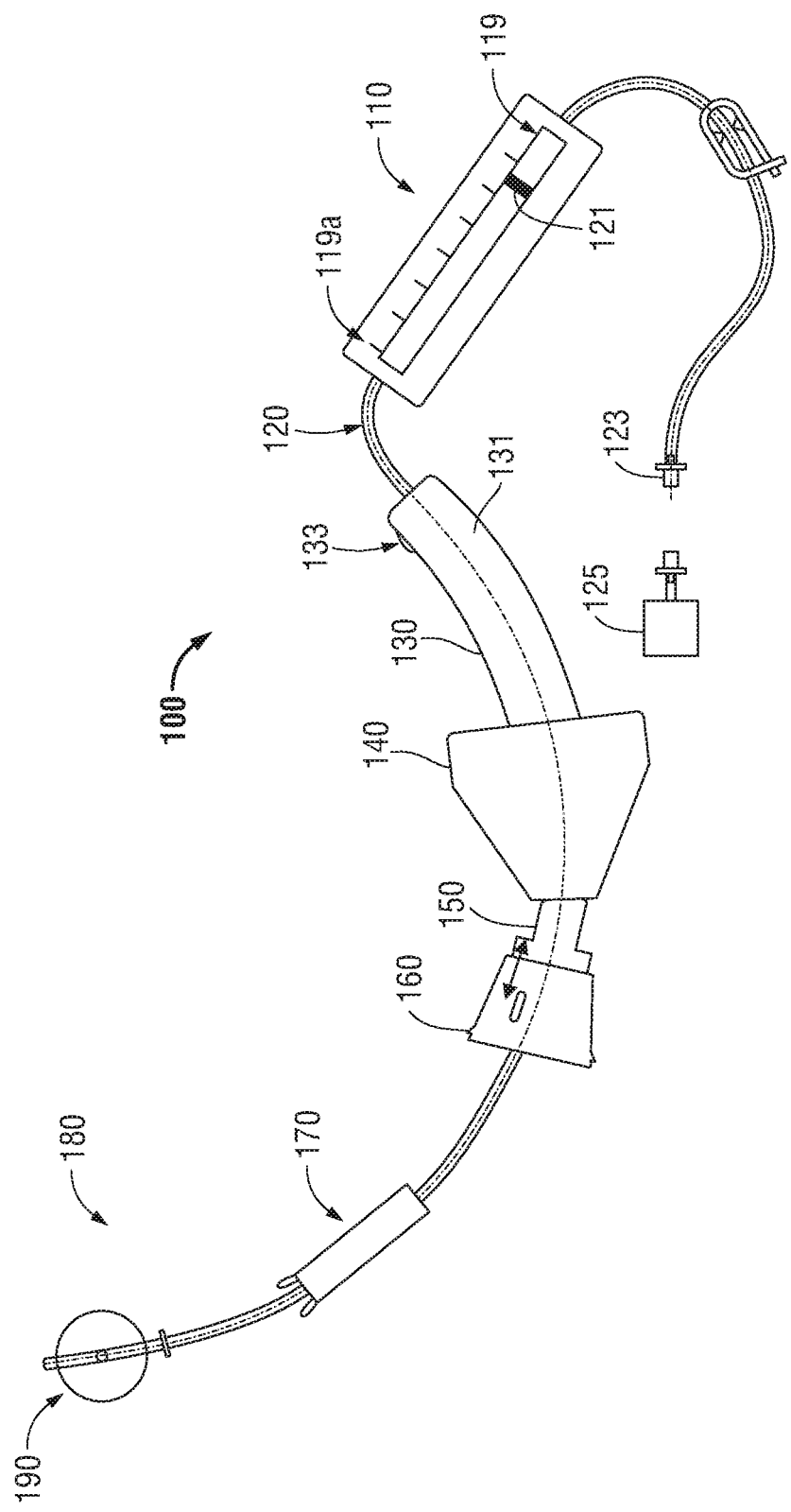
FIG. 1 is a side view of a uterine manipulator in accordance with the present disclosure.

Embodiments of the present disclosure are described in detail with reference to the drawings in which like reference numerals designate identical or corresponding elements in each of the several views. As used herein, the term "distal" refers to that portion of structure farther from the user, while the term "proximal" refers to that portion of structure closer to the user. As used herein, the term "clinician" refers to a doctor, nurse, or other care provider and may include support personnel. In the following description, well-known functions or constructions are not described in detail to avoid obscuring the present disclosure in unnecessary detail.

Referring to FIG. 1, a uterine manipulator is shown and generally identified by reference numeral 100. Uterine manipulator 100 is generally configured for insertion through the vaginal cavity "V" and into the uterus "U" and is used to mobilize and/or position the uterus "U" during pelvic surgical procedures (see FIGS. 4-6). Uterine manipulator 100 defines a central axis "Y-Y" and generally includes a handle 110 and a shaft 120 extending from handle 110. In embodiments, shaft 120 supports one or more of a slidable occluder shaft 130, an occluder 140, a shuttle 150, a cervical cup 160, a specimen containment system 170, and a uterine manipulating tip portion 180 including an inflatable balloon 190. Depending upon the desired configuration, uterine manipulator 100 may include some or all of these features.

Figure 4:
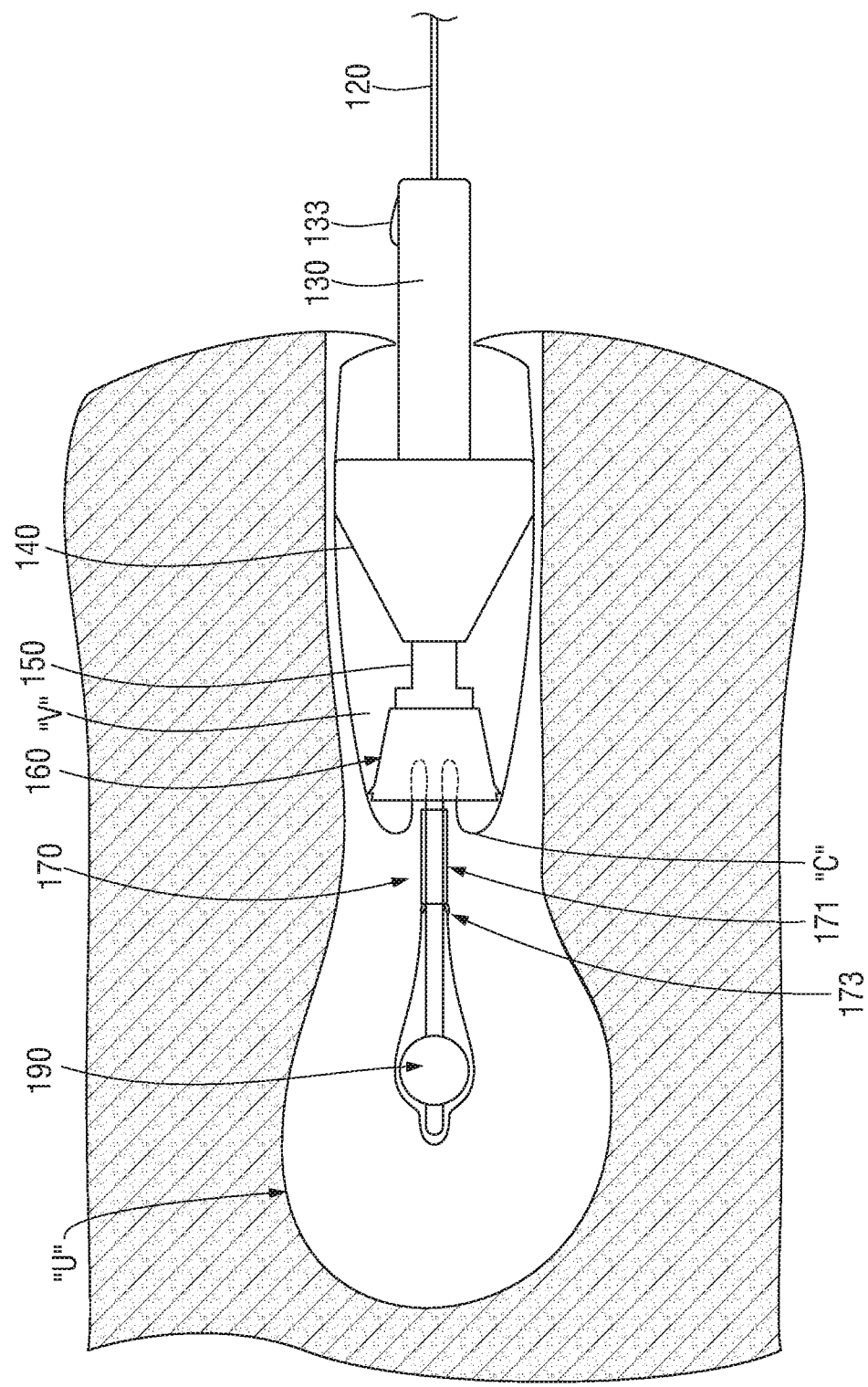
FIG. 4 is a schematic diagram of a distal end portion of the uterine manipulator of FIG. 1 disposed within a vaginal cavity.
Figure 5:
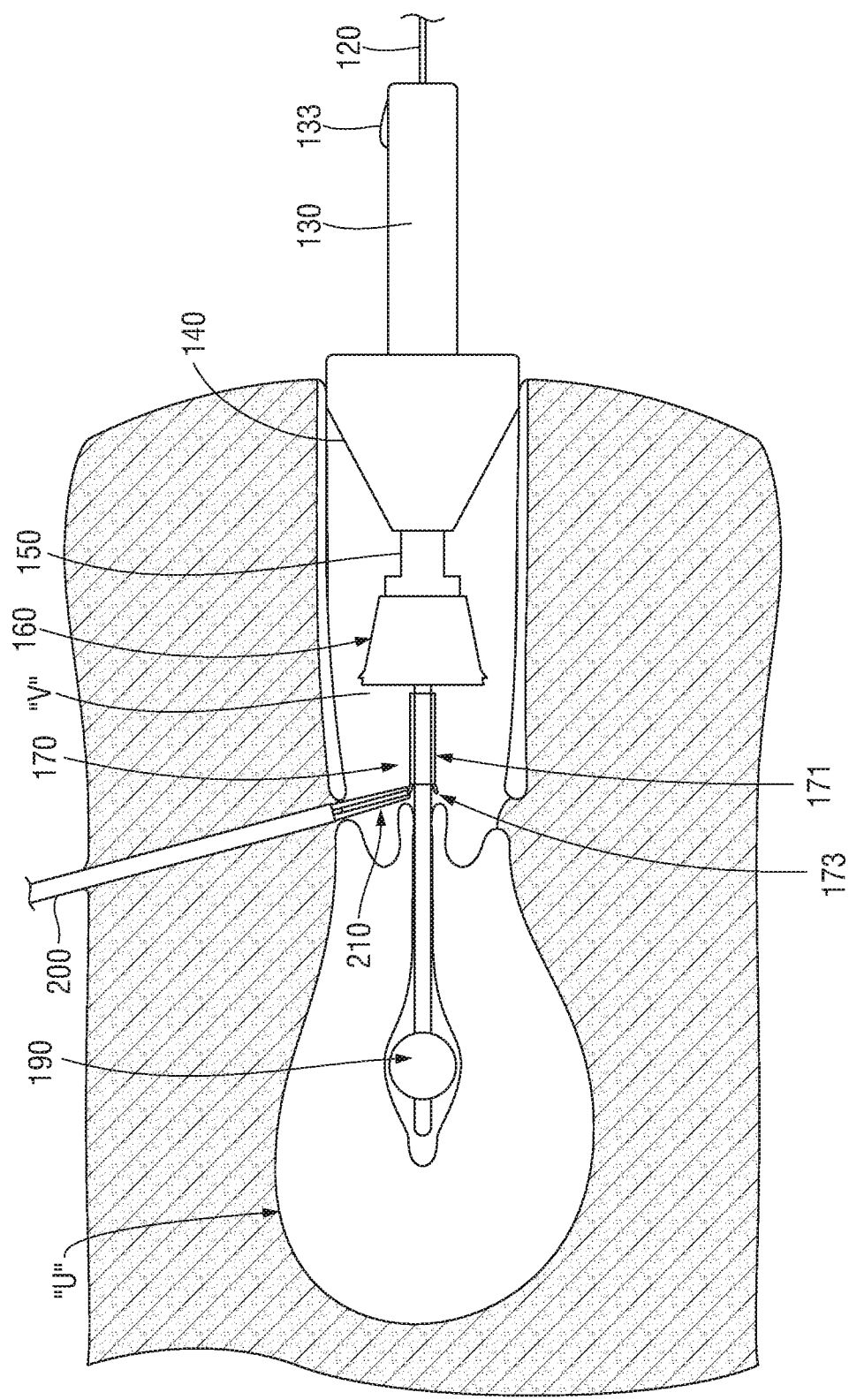
FIG. 5 is a schematic diagram of the distal end portion of the uterine manipulator of FIG. 4 disposed within the vaginal cavity with the specimen bag in an initial position.
Figure 6:
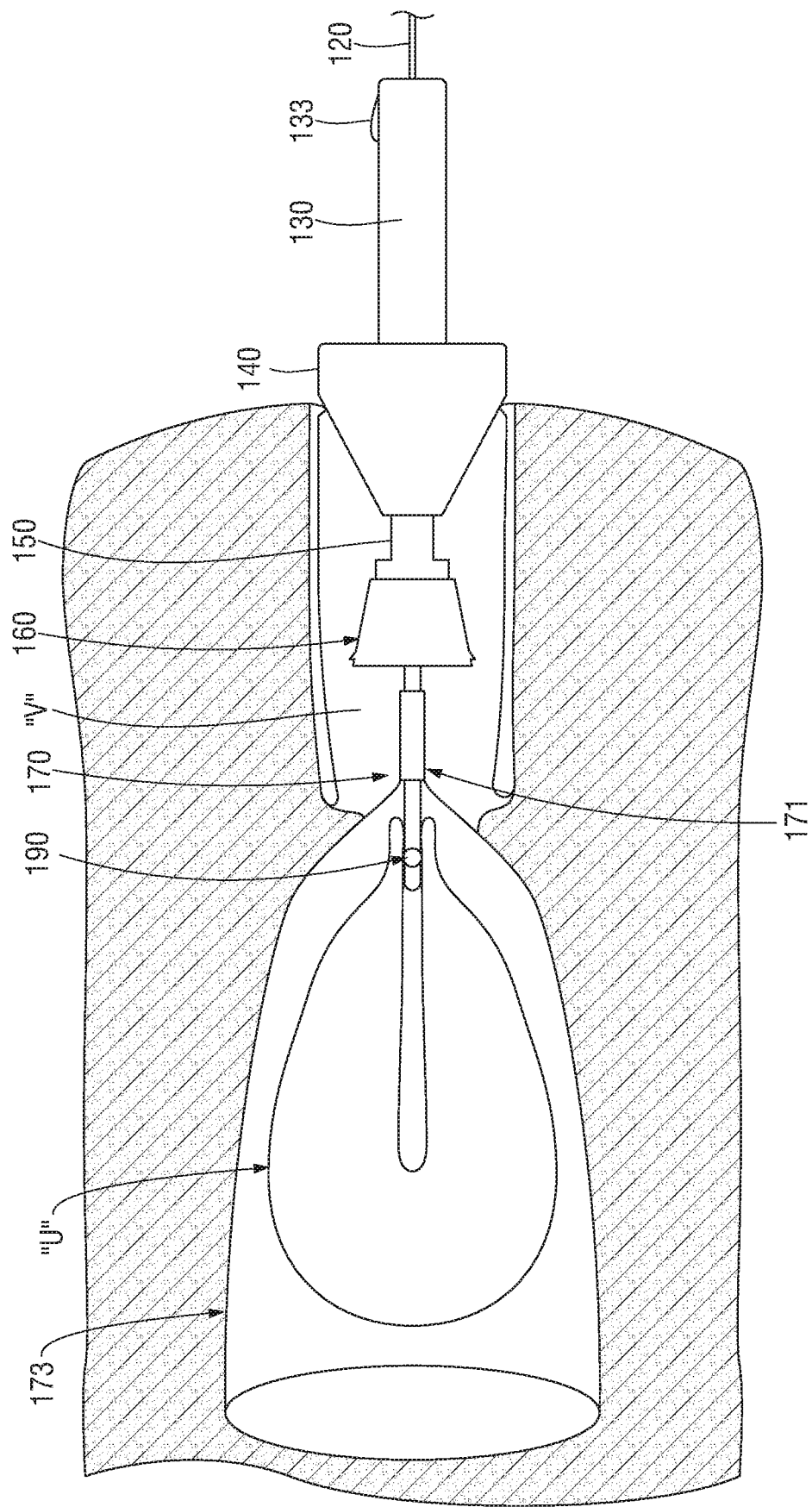
FIG. 6 is a schematic diagram of the distal end portion of the uterine manipulator of FIG. 4 disposed within the vaginal cavity with the specimen bag in a deployed position around a transected uterus.

Handle 110 of uterine manipulator 100 is configured to enable gripping and manipulation of uterine manipulator 100. Movement (e.g., axial, pivoting, rotation, etc.) of handle 110 causes uterine manipulating tip portion 180 to move for moving and/or positioning the uterus "U" (FIGS. 4-6), for example, for retroversion and anteversion of the uterus "U" (FIGS. 4-6). In some embodiments, as detailed below with respect to FIGS. 2A and 2B, handle 110 is operably coupled to shaft 120 to provide force-feedback information to a clinician during use of uterine manipulator 100. In other embodiments, the force-feedback feature is not provided and, instead, handle 110 is fixedly coupled to shaft 120.

Figure 2A:
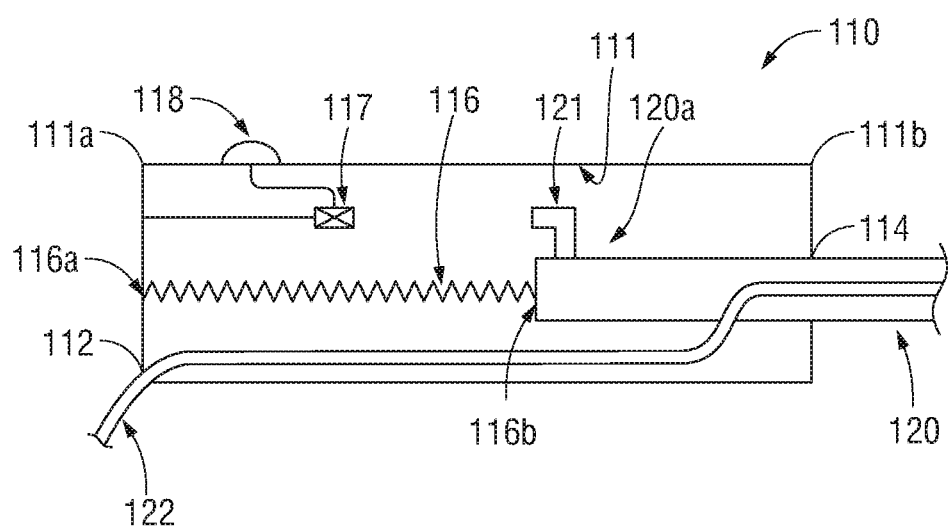
FIG. 2A is a longitudinal, cross-sectional view of a handle of the uterine manipulator of FIG. 1 in an unactuated position.
Figure 2B:
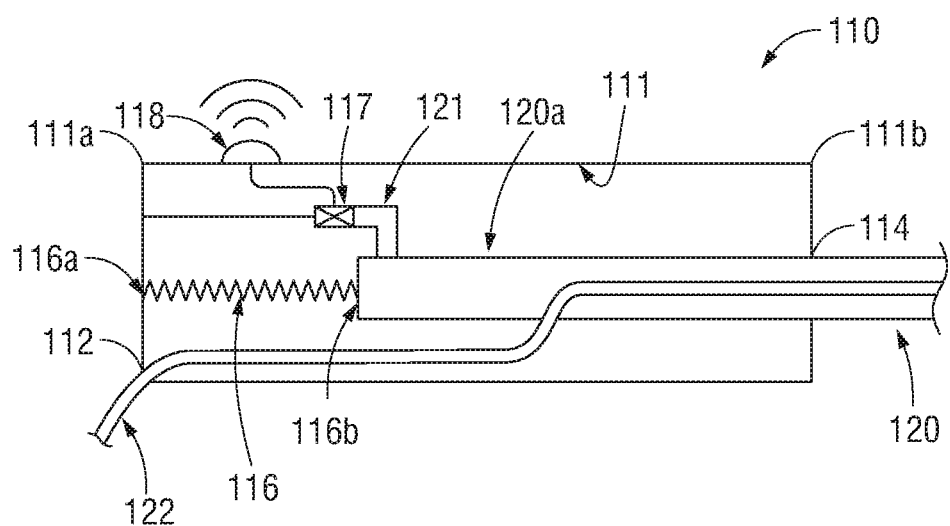
FIG. 2B is a longitudinal, cross-sectional view of the handle of the uterine manipulator of FIG. 1 in an actuated position.

With additional reference to FIGS. 2A and 2B, handle 110 includes a housing 111 defining a proximal end portion 111a and a distal end portion 111b. Proximal end portion 111a of housing 111 defines a first aperture 112 configured to receive a fluid conduit 122. Distal end portion 111b of housing 111 defines a second aperture 114 that slidably receives shaft 120. Housing 111 of handle 110 includes a biasing member 116 therein, which includes a first end portion 116a fixedly attached to proximal end portion 111a of housing 111 and a second end portion 116b fixedly attached to shaft 120. Biasing member 116 is compressible between proximal end portion 111a of housing 111 and shaft 120 and biases handle 110 relative to shaft 120 towards an at-rest orientation (FIG. 2A).

As a result of the above-detailed configuration, handle 110 is operably coupled to shaft 120 by way of biasing member 116. Thus, with cervical cup 160 of uterine manipulator 100 engaged about the cervix "C" (FIG. 4) (or another portion of uterine manipulator 100 contacting tissue), for example, application of distal force to handle 110 urges cervical cup 160 distally to apply pressure to the cervix "C" to displace the cervix "C." The cervix "C," in turn, provides an opposite proximal force on cervical cup 160. This opposite proximal force urges shaft 120 proximally such that biasing member 116 is compressed (FIG. 2B) between shaft 120 and proximal end portion 111a of housing 111, allowing handle 110 and shaft 120 to move relative to one another.

In embodiments, housing 111 of handle 110 further includes a sensor 117 configured to activate upon a specified application of force, as described below. Such sensors may include, for example, contact sensors, optical sensors, RFID sensors, Ferro-magnetic or magnetic tape sensors, strain gauges, or the like. An alert device 118 is operatively connected to sensor 117 to indicate to the clinician when the specified force has been reached, as also described below.

Additionally or alternatively, an outer surface of handle 110 may include a window 119 (FIG. 1) and a plurality of markings 119a disposed along a length of window 119. Window 119 is configured to enable viewing inside housing 111 to provide an indication of the force applied to handle 110, as described below.

Continuing with reference to FIGS. 1-2B, shaft 120 extends distally from handle 110 and is configured for insertion through the vaginal cavity "V" into the uterus "U" (see FIGS. 4-6). A proximal end portion 120a of shaft 120 is slidably disposed within housing 111 of handle 110, in embodiments where the force-feedback feature is provided. In such embodiments, an indicator 121 is disposed on proximal end portion 120a of shaft 120. Indicator 121 is viewable through window 119 of handle 110 and/or is configured to contact sensor 117 once a specified force has been applied to handle 110, which triggers alert device 118, as described below.

Indicator 121, more specifically, is moved through window 119 and/or relative to sensor 117 as handle 110 and shaft 120 are moved relative to one another, e.g., in response to distal urging of handle 110 and opposite proximal force urging shaft 120 proximally to compress biasing member 116, as detailed above. Thus, the position of indicator 121 correlates to the force applied to tissue, e.g., via cervical cup 160. With respect to window 119, markings 119*a* may indicate a force measurement (e.g., in psi and/or kg/cm$^2$) or may indicate a relative amount of force (e.g., 1, 2, 3, 4, or 5), such that the position of indicator 121 within window 119 enables the clinician to identify the nearest marking 119*a* and, thus, ascertain the force measurement or relative amount of force applied to tissue. With respect to sensor 117, indicator 121 is moved into contact with sensor 117 when the force applied to tissue reaches a threshold value, thus indicating to the clinician that the force applied to tissue has reached the threshold force. Accordingly, the clinician can adjust the force applied to tissue, as necessary, by increasingly or decreasingly urging handle 110 distally. Further, by coupling biasing member 116 between handle 110 and shaft 120, a more consistent force can be applied to tissue.

Fluid conduit 122 extends into housing 111 of handle 110 and through shaft 120 and is connected to port 123 at a proximal end portion thereof and to inflatable balloon 190 at a distal end portion thereof. Port 123 couples to an inflation source 125 for delivering inflation fluid (e.g., saline, air, or the like) from inflation source 125 through fluid conduit 122 to inflatable balloon 190, such that inflatable balloon 190 may be inflated with the inflation fluid.

Slidable occluder shaft 130 is positioned about shaft 120 and generally defines an elongate body 131 including a button 133. Button 133 is selectively actuatable to enable movement of slidable occluder shaft 130 proximally and/or distally along shaft 120.

Occluder 140 is slidably disposed about shaft 120 distal of slidable occluder shaft 130. Occluder 140 may include a compressible foam material that can be compressed during insertion into the vagina cavity "V" (FIGS. 4-6) to occlude the vaginal cavity "V" (FIGS. 4-6) and prevent the loss of pneumoperitoneum, e.g., during a colpotomy procedure.

Shuttle 150 is slidably disposed about shaft 120 distal of occluder 140. Cervical cup 160 is slidably disposed about shaft 120 distal of shuttle 150. Cervical cup 160 generally defines a cup-like configuration configured to abut and envelope the cervix "C," e.g., for displacing the cervix "C" away from the ureters, bladder, and rectum and/or for defining cervical points of reference for a colpotomy incision. Shuttle 150 may be selectively coupled to cervical cup 160 to enable cervical cup 160 and shuttle 150 to move together.

Figure 3A:
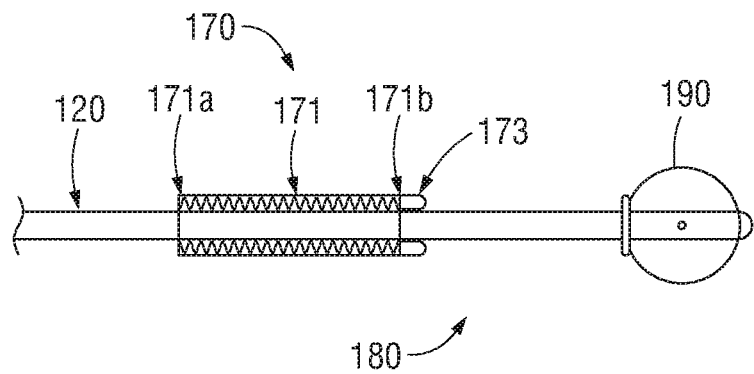
FIG. 3A is a longitudinal, cross-sectional view of a distal end portion of the uterine manipulator of FIG. 1 illustrating a specimen containment system thereof.
Figure 3B:
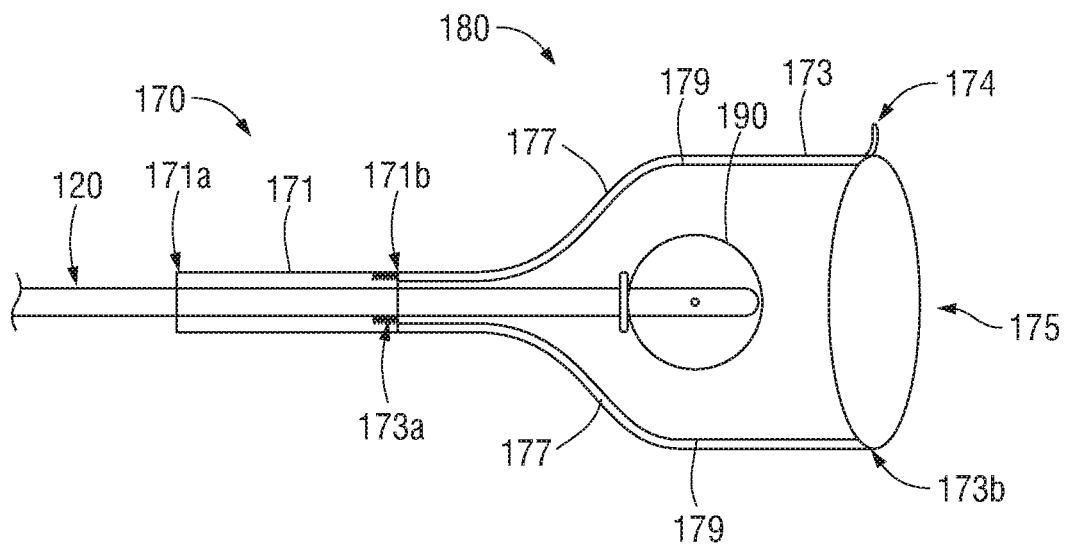
FIG. 3B is a longitudinal, cross-sectional view of the distal end portion of the uterine manipulator of FIG. 3A including a specimen bag of the specimen containment system in a deployed position.

With reference to FIGS. 1, 3A, and 3B, in some embodiments, uterine manipulator 100 includes specimen containment system 170. Specimen containment system 170 includes a sleeve 171 supported on shaft 120 of uterine manipulator 100. Sleeve 171 generally defines an elongate tubular shape and is configured to extend through the vaginal cavity "V" (FIGS. 4-6). Sleeve 171 includes a proximal end portion 171*a* and a distal end portion 171*b*. Sleeve 171 may be movable along shaft 120 or may be fixed relative thereto. Sleeve 171 may be formed from any suitable material such as stainless steel, plastic, titanium, or the like.

A specimen containment bag 173 is disposed within sleeve 171. Specimen containment bag 173 includes a proximal end portion 173*a* and an open distal end portion 173*b*. Specimen containment bag 173 may be formed from any suitable material. In particular, specimen containment bag 173 may be formed from a transparent, tear-resistant, and/or stretchable material to enable visualization into specimen containment bag 173 from the exterior thereof, inhibit tearing, and/or facilitate manipulation of specimen containment bag 173, tissue specimen(s), and/or surgical instrumentation during use.

Open proximal end portion 173*a* of specimen containment bag 173 may define a closable configuration to facilitate sealed closure thereof, such as, for example, by way of suture, cinch cord, tying-off, or other suitable mechanism or method. Open distal end portion 173*b* of specimen containment bag 173 includes a grasping tab 174 to facilitate manipulation of the open distal end portion 173*b*. A reinforced rim 175 surrounds the open distal end portion 173*b*. Rim 175 may be formed from a spring-metal, e.g., nitinol, or other suitable material that is resiliently flexible, returning to a pre-determined shape in the absence of external forces applied thereto. This configuration allows rim 175 to be flexed or otherwise re-positioned to enable receipt of open distal end portion 173*b* of specimen containment bag 173 within sleeve 171. Specimen containment bag may also include a plurality of elongated pockets 177 disposed on an interior surface thereof. Free distal end portions of resilient fingers 179 are disposed in elongated pockets 177. Resilient fingers 179 may be formed from a spring-metal, e.g., nitinol, or other suitable material that is resiliently flexible, returning to a pre-determined shape in the absence of external forces applied thereto. Resilient fingers 179 may be engaged to shaft 120 at the proximal end portions thereof, may be engaged to a deployment shaft (not shown) disposed about shaft 120, or may be engaged to a proximal ring (not shown) associated with specimen containment bag 173. As a result of the above-detailed configuration, upon deployment of specimen bag 173 from sleeve 171, rim 175 and/or resilient fingers 179 are returned under bias towards their pre-determined shapes, cause specimen containment bag 173 to bias toward an open condition (FIG. 3B).

Specimen containment bag 173 is configured for positioning, in the initial position (FIG. 3A), between proximal end portion 171*a* and distal portion 171*b* of sleeve 171, although a portion of specimen containment bag 173 may extend distally or proximally from sleeve 171. In the deployed position (FIG. 3B), specimen containment bag 173 extends distally from sleeve 171 into, e.g., vaginal cavity "V" and around a transected uterus "U" (FIG. 6). In order to deploy specimen containment bag 173, sleeve 171 may be translated proximally along shaft 120 and relative to specimen containment bag 173, e.g., via actuation of a deployment shaft (not shown). Alternatively, a deployment shaft (not shown) may be translated distally about shaft 120 and relative to sleeve 171 to urge containment bag 173 from sleeve 171. As another alternatively, specimen containment bag 173 may be manually deployed, e.g., pushed or pulled, from sleeve 171. Other suitable configurations and/or features for selective deployment of specimen containment bag 173 are also contemplated.

In use, with reference to FIGS. 4-6, during, for example, a laparoscopic hysterectomy, the abdominal cavity is insufflated with a gas, or pneumoperitoneum, to distend and separate the abdominal wall from the uterus, such that the clinician can adequately view the surgical site and perform, e.g., a colpotomy procedure. The use of uterine manipulator 100 described below includes all of the features of the various embodiments detailed above. However, it is understood that, in embodiments, all of such features and uses need not be provided.

Initially, uterine manipulating tip portion 180 of uterine manipulator 100 is advanced distally through the vaginal cavity "V" of a patient until cervical cup 160 is in abutment with the cervix "C" and uterine manipulating tip portion 180 is placed within the uterus "U." The clinician applies a sufficient distal force to handle 110 of uterine manipulator 100 in order mobilize the cervix "C" away from the ureters, which will allow the clinician to make the colpotomy incision and separate the uterus "U" from the vagina. In order to determine the force applied to the cervix "C," the clinician monitors indicator 121 through window 119 of handle 110 relative to the plurality of markings 119a that are disposed on the outer surface of handle 110, as detailed above.

In addition or as an alternative to using the force markings 119a and indicator 121 to determine the force applied to the cervix "C" through window 119, sensor 117 may provide an indication that a threshold force has been applied to the cervix "C." Specifically, as detailed above, when the threshold force is reached, indicator 121 contacts sensor 117 causing alert device 118 to activate and elicit an auditory tone, a tactile indication (e.g., vibration), and/or a visual cue (e.g., flashing LED light). As such, uterine manipulator 100 provides a continuous and/or threshold indication of the force applied to the cervix "C."

The clinician may continue to move handle 110 to cause movement of uterine manipulating tip portion 180, which causes movement of the uterus "U." Specifically, movement of handle 110 causes movement of uterine manipulating tip portion 130 for retroversion and anteversion of the uterus "U." Once the cervix "C" is mobilized away from the ureters, bladder, and rectum with cervical cup 160, the clinician can make the colpotomy incision to separate the uterus "U" from the vagina.

With reference to FIG. 5, with the uterus "U" separated from the vagina, the uterine manipulator 100 may be positioned such that the specimen containment system 170 is located proximally of the uterus "U." The clinician may then insert a grasping device 200 including a pair of jaws 210 through a separate port or incision (FIG. 5) to grasp and pull the rim 175 of the specimen containment bag 173 out of the sleeve 171 such that the specimen containment bag 173 moves from the initial position (FIG. 5) to the deployed position (FIG. 6) to surround the uterus "U." Additionally or alternatively, handle 110 may be manipulated to move shaft 120 proximally and/or distally such that the uterus "U" provides counter-traction against the specimen containment system 170 to cause specimen bag 173 of specimen containment system 170 to deploy from sleeve 171. Rim 175 and resilient fingers 179 of specimen containment bag 173 cause specimen containment bag 173 to expand outwardly once removed or deployed from sleeve 171. As an alternative to manual deployment, an actuation shaft (not shown) may be translated relative to shaft 120, specimen containment bag 173, and/or sleeve 171 to deploy specimen containment bag 173 therefrom, as noted above.

Once the specimen containment bag 173 is deployed above the uterus "U," uterine manipulator 100 may be withdrawn from the vaginal cavity "V," leaving specimen containment bag 173 in place around the transected uterus "U." Alternatively, in embodiments where sleeve 171 is fixedly attached to specimen bag 173, the combination of sleeve 171 and specimen bag 173 may remain in the vaginal cavity "V" as the remainder of the uterine manipulator 100 is withdrawn from the vaginal cavity "V." One or both ends of the specimen containment bag 173 may then be closed and/or externalized. The transected uterus "U" can then be morcellated from within the specimen containment bag 173, if needed, and remaining end(s) of the specimen containment bag 173 may then be closed and/or externalized. Because the tissue specimen is contained within the specimen bag 173 during morcellation, the seeding of cancer cells is prevented. Finally, the specimen containment bag 173 is removed.

Figure 7:
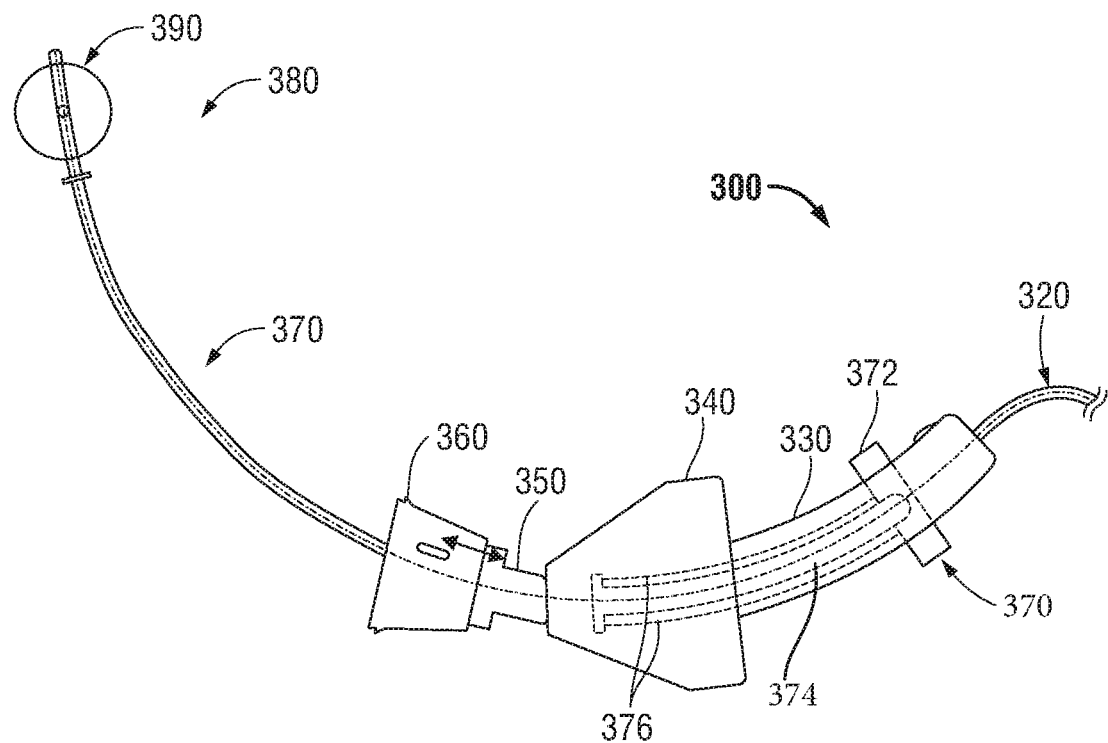
FIG. 7 is a side view of a distal portion of another uterine manipulator in accordance with the present disclosure.

Turning to FIG. 7, another uterine manipulator 300 provided in accordance with the present disclosure is shown. Uterine manipulator 300 may include any of the features of uterine manipulator 100 (FIG. 1) and may be used similarly as uterine manipulator 100 (FIG. 1), except where specifically contradicted below. Likewise, uterine manipulator 100 (FIG. 1) may include any of the features of uterine manipulator 300. Thus, only differences therebetween will be described in detail below. Uterine manipulator 300 generally includes a handle (not shown) and a shaft 320 extending from the handle (not shown). Shaft 320 supports an outer sleeve 330, an occluder 340, a cervical cup 360 attached to occluder 340 (with or without a shuttle 350 therebetween), a specimen containment system 370, and a uterine manipulating tip portion 380 including an inflatable balloon 390. Depending upon the desired configuration, uterine manipulator 300 may include some or all of these features.

Specimen containment system 370 is selectively deployable from outer sleeve 330 (which functions as the sleeve of the specimen containment system 370, similar to the sleeve of specimen containment system detailed above (see FIGS. 1, 3A, and 3B)), and includes an actuator 372, e.g., a slider, operably disposed on outer sleeve 330, a specimen containment bag 374 initially disposed within outer sleeve 330 and about shaft 320, and a plurality of resilient fingers 376 operably coupled to specimen containment bag 374. Except as explicitly contradicted below, specimen containment system 370 and the components thereof may include any of the features detailed above with respect to specimen containment system 170 (see FIGS. 1, 3A, and 3B). Specimen containment system 370 is initially disposed in a retracted position, as illustrated in FIG. 1.

Figure 8A:
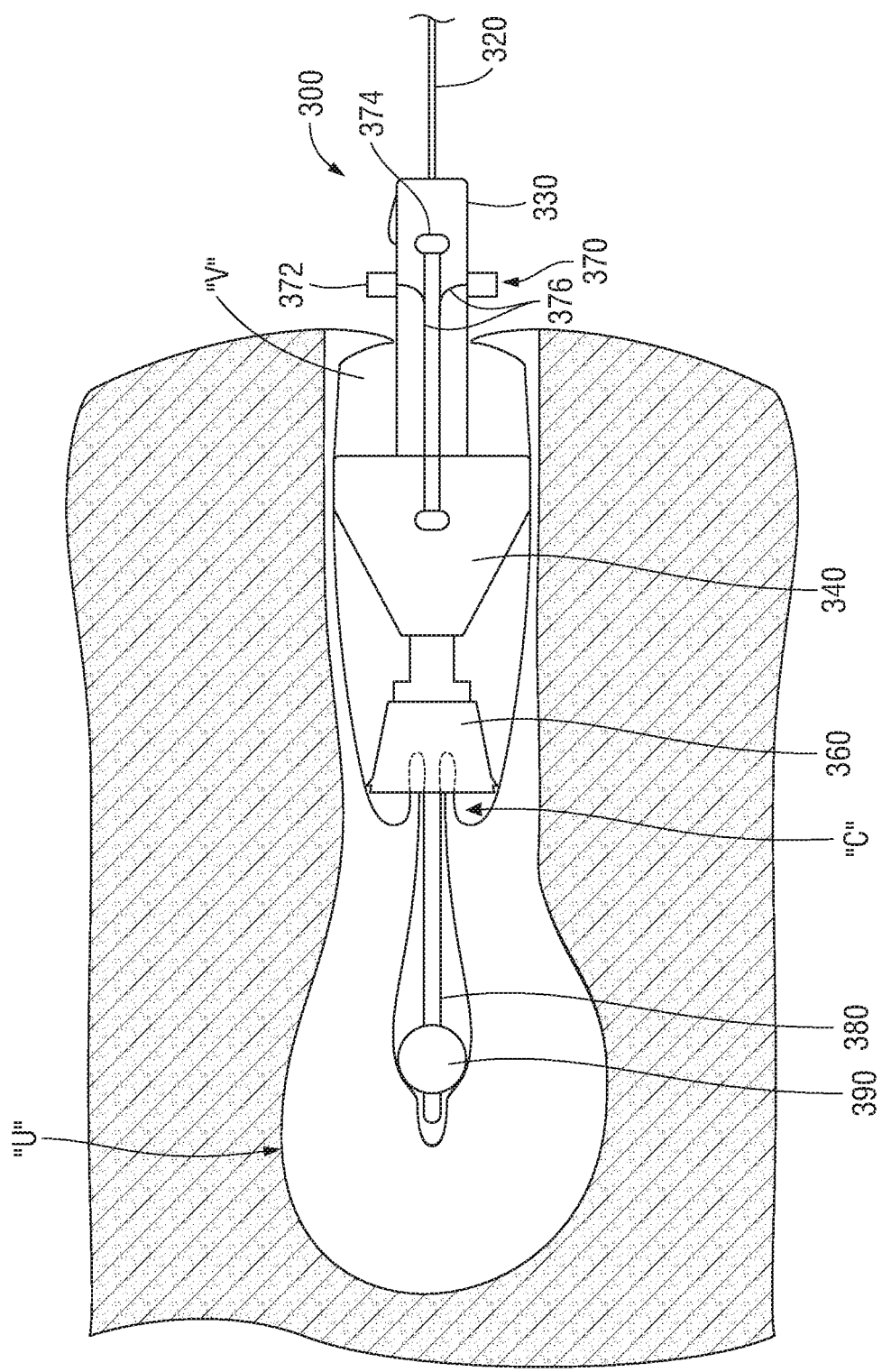
FIGS. 8A-8D are schematic diagrams of the distal end of the uterine manipulator of FIG. 7 illustrating use thereof.
Figure 8B:
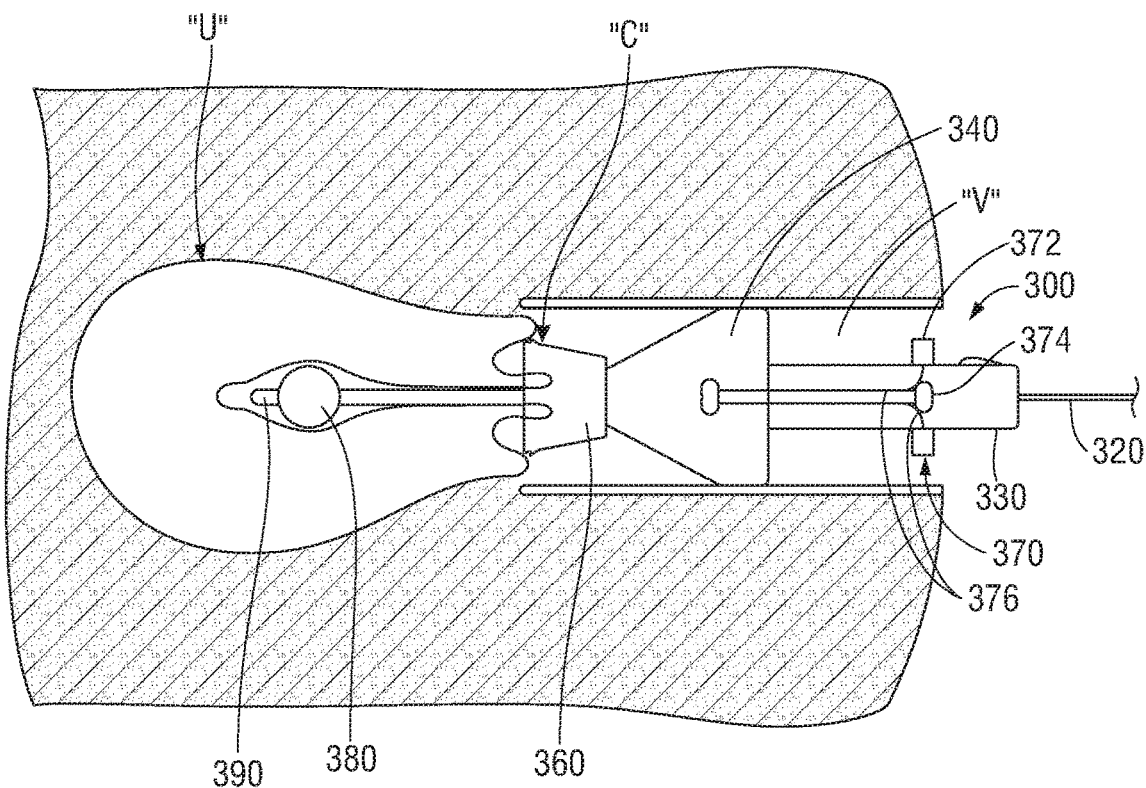

With reference to FIGS. 8A-8D, in conjunction with FIG. 7, the use of uterine manipulator 300 is detailed. Initially, as shown in FIG. 8A, uterine manipulator 300 is advanced distally through the vaginal cavity "V" until cervical cup 360 is in abutment with the cervix "C" and uterine manipulating tip portion 380 extends through the cervix "C" into the uterus "U." Referring to FIG. 8B, uterine manipulator 300 is maneuvered to mobilize the cervix "C" away from the ureters, bladder, and rectum using the cervical cup 360, thus enabling the clinician to make the colpotomy incision to separate the uterus "U" from the vagina.

Figure 8C:
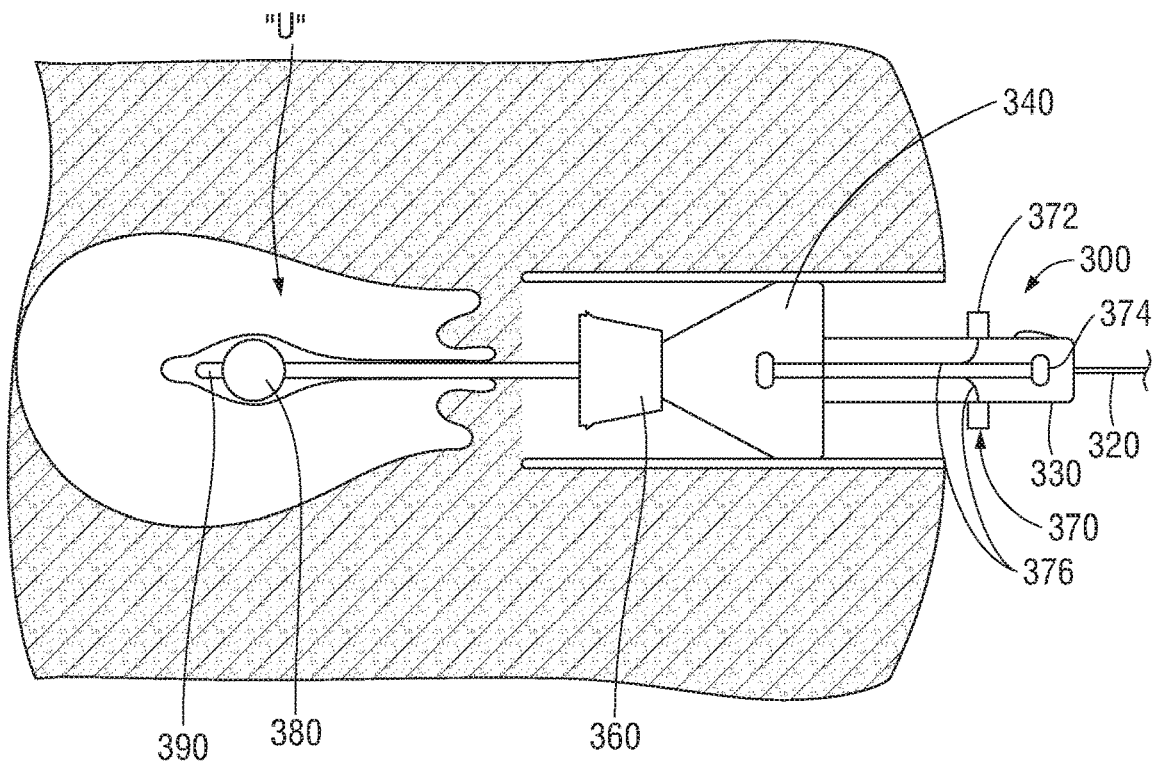

With reference to FIG. 8C, with the uterus "U" separated from the vagina, uterine manipulating tip portion 380 of uterine manipulator 300 is advanced distally and/or cervical cup 360 and occluder 340 are retracted proximally to thereby crease spacing between the uterus "U" and the vagina and other surrounding tissue(s).

Figure 8D:
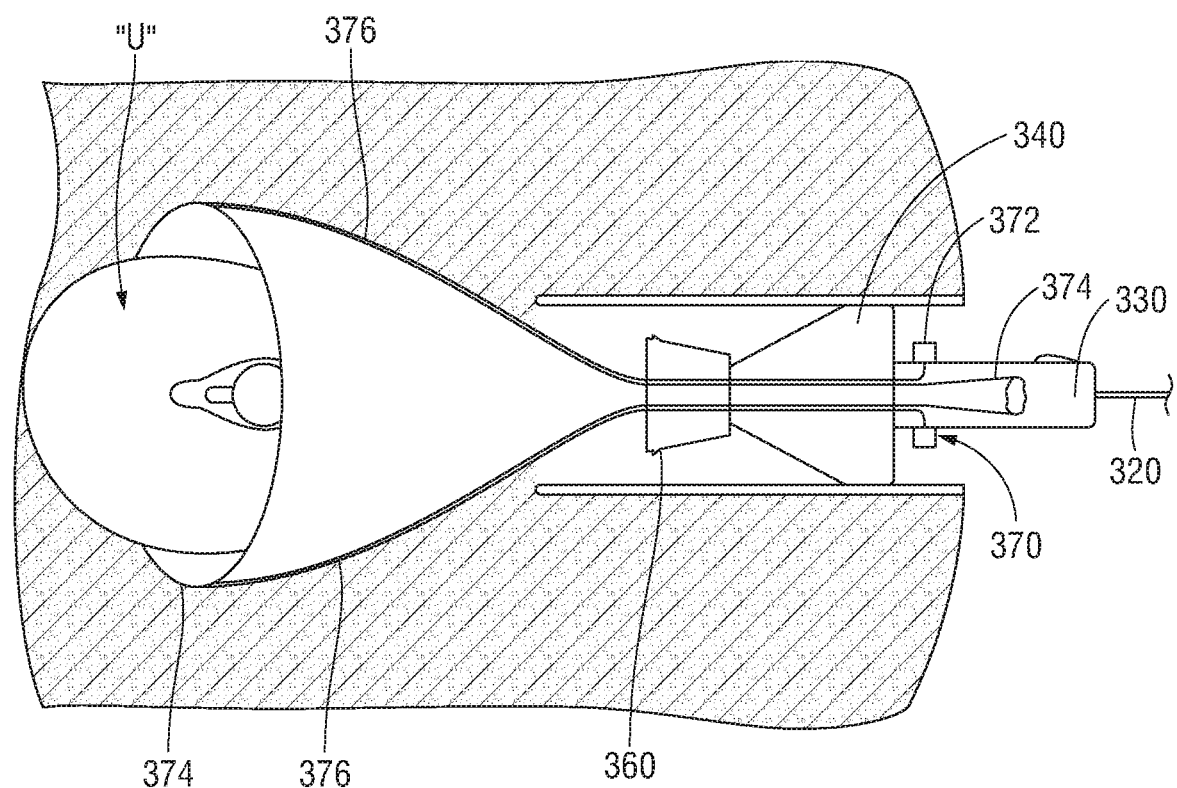

Turning now to FIG. 8D, with spacing defined between the uterus "U" and the vagina and other surrounding tissue(s), specimen containment bag 374 may be deployed. Specimen containment bag 374 is deployed by sliding actuator 372 distally along outer sleeve 330. Actuator 372 is coupled to resilient fingers 376 such that distal advancement of actuator 372 advances resilient fingers 376 distally. Resilient fingers 376, in turn, are coupled to specimen containment bag 374, similarly as detailed above, such that distal advancement of resilient fingers 376 urges an end of specimen containment bag 374 distally. Eventually, fingers 376 and the end of specimen containment bag 374 extend distally from outer sleeve 330, occlude 340, and cervical cup 360, thus allowing resilient fingers 376 to spring open and widen the open end of specimen containment bag 374 within the spacing defined between the uterus "U" and the vagina and other surrounding tissue(s). Further distal advancement of fingers 376 and the end of specimen containment bag 374 enables receipt of the uterus "U" within specimen containment bag 374.

With the uterus "U" contained within specimen containment bag 374, uterine manipulator 300 (or portions thereof) may be withdrawn. One or both ends of the specimen containment bag 374 may then be closed and/or externalized. The uterus "U" can then be morcellated from within the specimen containment bag 374, if needed, and remaining end(s) of the specimen containment bag 374 may then be closed and/or externalized. Finally, the specimen containment bag 374 is removed.

Figure 9:
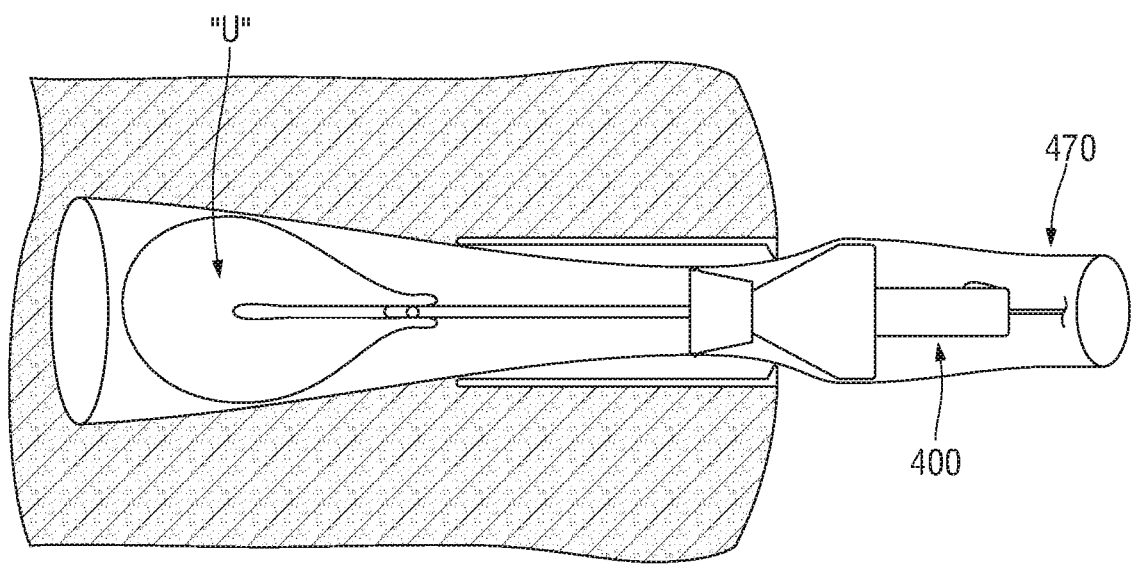
FIG. 9 is a schematic diagram illustrating a uterine manipulator and a specimen bag configured for use therewith in accordance with the present disclosure.

Referring to FIG. 9, in embodiments, rather than deploying the specimen containment bag from about the uterine manipulator, a uterine manipulator 400 and specimen containment bag 470 may be provided and configured such that the specimen containment bag 470 is configured to fully surround the uterine manipulator 400. In this manner, specimen containment bag 470 may be deployed about the uterine manipulator 400 and the uterus "U," as illustrated in FIG. 9. Uterine manipulator 400 may otherwise be configured similarly to uterine manipulators 100 and/or 300 (FIGS. 1 and 7, respectively), detailed above.

It should be appreciated that devices, systems, and methods described herein may be used for any type of surgical procedure and are not limited to laparoscopic hysterectomy procedures.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A uterine manipulator, comprising:
a handle assembly;
a shaft extending distally from the handle assembly, the shaft defining a longitudinal axis;
an end effector assembly disposed at a distal end portion of the shaft, the end effector assembly including a cervical cup and a distal tip extending distally from the cervical cup;
a specimen containment system supported on the shaft between the handle assembly and the end effector assembly, the specimen containment system including:
a sleeve having a proximal end portion and a distal end portion, the sleeve circumferentially disposed about an exterior surface of the shaft; and
a specimen containment bag defining a first end portion, a second end portion, and an open interior portion therebetween, the specimen containment bag supported about the exterior surface of the shaft, the specimen containment bag movable from an initial position, wherein the specimen containment bag is disposed within the sleeve, to a deployed position, wherein the open interior portion of the specimen containment bag expands radially outward and extends distally away from the sleeve along the longitudinal axis.

2. The uterine manipulator according to claim 1, wherein the second end portion of the specimen containment bag includes a reinforced rim.

3. The uterine manipulator according to claim 2, wherein in the initial position, at least a portion of the reinforced rim is disposed within the sleeve and wherein, in the deployed position, the reinforced rim is disposed externally of the sleeve.

4. The uterine manipulator according to claim 2, wherein the reinforced rim includes a resiliently flexible material.

5. The uterine manipulator according to claim 4, wherein the reinforced rim is returned under bias towards an at-rest position upon movement of the specimen containment bag to the deployed position.

6. The uterine manipulator according to claim 1, wherein the second end portion of the specimen containment bag includes a grasping tab.

7. The uterine manipulator according to claim 1, wherein the specimen containment bag includes a plurality of elongated pockets disposed on an interior surface thereof, each pocket including a resilient finger therein configured to bias the specimen containment bag toward an open condition.

8. The uterine manipulator according to claim 1, wherein the specimen containment bag is formed from at least one of a transparent, tear-resistant, or stretchable material.

9. The uterine manipulator according to claim 1, further comprising a shuttle slidably supported on the shaft and selectively coupled to the cervical cup.

10. The uterine manipulator according to claim 1, further comprising an inflatable balloon supported on the distal end portion of the shaft.

11. The uterine manipulator according to claim 1, further comprising an occluder slidably supported on the shaft.

* * * * *